United States Patent
Falwell et al.

(10) Patent No.: US 8,527,027 B2
(45) Date of Patent: *Sep. 3, 2013

(54) METHOD AND APPARATUS FOR MAPPING AND/OR ABLATION OF CARDIAC TISSUE

(75) Inventors: Gary S. Falwell, Moultonborough, NH (US); Erik Brown, Brea, CA (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/456,573

(22) Filed: Apr. 26, 2012

(65) Prior Publication Data

US 2012/0209262 A1 Aug. 16, 2012

Related U.S. Application Data

(63) Continuation of application No. 11/596,403, filed as application No. PCT/US2005/017337 on May 17, 2005, now Pat. No. 8,249,685.

(60) Provisional application No. 60/571,821, filed on May 17, 2004.

(51) Int. Cl.
*A61B 5/0402* (2006.01)
*A61B 18/14* (2006.01)

(52) U.S. Cl.
USPC .............................. 600/374; 600/373; 606/41

(58) Field of Classification Search
USPC ................. 600/374, 372, 373, 381, 393, 509; 606/41
See application file for complete search history.

(56) References Cited

U.S. PATENT DOCUMENTS

| | | | |
|---|---|---|---|
| 3,996,938 A | 12/1976 | Clark, III |
| 4,660,571 A | 4/1987 | Hess et al. |
| 4,664,120 A | 5/1987 | Hess |
| 4,699,147 A | 10/1987 | Chilson et al. |
| 4,709,698 A | 12/1987 | Johnston et al. |
| 4,921,484 A | 5/1990 | Hillstead |
| 4,940,064 A | 7/1990 | Desai |
| 4,998,539 A | 3/1991 | Delsanti |
| 5,010,894 A | 4/1991 | Edhag |
| 5,100,423 A | 3/1992 | Fearnot |
| 5,190,542 A | 3/1993 | Nakao et al. |
| 5,215,103 A | 6/1993 | Desai |
| 5,231,995 A | 8/1993 | Desai |
| 5,255,679 A | 10/1993 | Imran |
| 5,311,866 A | 5/1994 | Kagan |

(Continued)

FOREIGN PATENT DOCUMENTS

| | | |
|---|---|---|
| EP | 0 428 279 | 4/1991 |
| EP | 0 771 547 A2 | 7/1997 |

(Continued)

*Primary Examiner* — Lee S Cohen
*Assistant Examiner* — Erin M Cardinal
(74) *Attorney, Agent, or Firm* — Wolf, Greenfield & Sacks, P.C.

(57) ABSTRACT

An apparatus for mapping and/or ablating tissue includes a braided conductive member that that may be inverted to provide a ring-shaped surface. When a distal tip of the braided conductive member is retracted within the braided conductive member, the lack of a protrusion allows the ring-shaped surface to contact a tissue wall such as a cardiac wall. In an undeployed configuration, the braided conductive member is longitudinally extended, and in a deployed configuration, the distal end of the braided conductive member is retracted to invert the braided conductive member.

21 Claims, 4 Drawing Sheets

(56) References Cited

U.S. PATENT DOCUMENTS

| | | | |
|---|---|---|---|
| 5,313,943 | A | 5/1994 | Houser et al. |
| 5,324,284 | A | 6/1994 | Imran |
| 5,365,926 | A | 11/1994 | Desai |
| 5,383,852 | A | 1/1995 | Stevens-Wright et al. |
| 5,397,339 | A | 3/1995 | Desai |
| 5,397,341 | A | 3/1995 | Hirschberg et al. |
| 5,400,783 | A | 3/1995 | Pomeranz et al. |
| 5,403,311 | A | 4/1995 | Abele et al. |
| 5,409,000 | A | 4/1995 | Imran |
| 5,415,166 | A | 5/1995 | Imran |
| 5,433,198 | A | 7/1995 | Desai |
| 5,465,717 | A | 11/1995 | Imran et al. |
| 5,476,495 | A | 12/1995 | Kordis et al. |
| 5,549,108 | A | 8/1996 | Edwards et al. |
| 5,575,810 | A | 11/1996 | Swanson et al. |
| 5,611,777 | A | 3/1997 | Bowden et al. |
| 5,636,634 | A | 6/1997 | Kordis et al. |
| 5,653,684 | A | 8/1997 | Laptewicz et al. |
| 5,680,860 | A | 10/1997 | Imran |
| 5,681,280 | A | 10/1997 | Bowe et al. |
| 5,702,438 | A | 12/1997 | Avitall |
| 5,722,403 | A | 3/1998 | McGee et al. |
| 5,725,552 | A | 3/1998 | Kotula et al. |
| 5,730,128 | A | 3/1998 | Pomeranz et al. |
| 5,738,683 | A | 4/1998 | Osypka |
| 5,800,482 | A | 9/1998 | Pomeranz et al. |
| 5,813,997 | A | 9/1998 | Quiachon et al. |
| 5,836,947 | A | 11/1998 | Fleischman et al. |
| 5,860,974 | A | 1/1999 | Abele |
| 5,868,706 | A | 2/1999 | Cox |
| 5,879,348 | A | 3/1999 | Owens et al. |
| 5,891,136 | A | 4/1999 | McGee et al. |
| 5,893,885 | A | 4/1999 | Webster, Jr. |
| 5,904,698 | A | 5/1999 | Thomas et al. |
| 5,916,213 | A | 6/1999 | Haissaguerre et al. |
| 5,921,982 | A | 7/1999 | Lesh et al. |
| 5,928,260 | A | 7/1999 | Chin et al. |
| 5,931,863 | A | 8/1999 | Griffin, III et al. |
| 5,944,738 | A | 8/1999 | Amplatz et al. |
| 5,951,471 | A | 9/1999 | de la Rama et al. |
| 5,968,040 | A | 10/1999 | Swanson et al. |
| 5,997,536 | A | 12/1999 | Osswald et al. |
| 6,001,093 | A | 12/1999 | Swanson et al. |
| 6,014,581 | A | 1/2000 | Whayne et al. |
| 6,014,590 | A | 1/2000 | Whayne et al. |
| 6,023,638 | A | 2/2000 | Swanson |
| 6,029,671 | A | 2/2000 | Stevens et al. |
| 6,052,607 | A | 4/2000 | Edwards et al. |
| 6,071,282 | A | 6/2000 | Fleischman |
| 6,119,030 | A | 9/2000 | Morency |
| 6,142,993 | A | 11/2000 | Whayne et al. |
| 6,146,379 | A | 11/2000 | Fleischman et al. |
| 6,163,716 | A | 12/2000 | Edwards et al. |
| 6,240,307 | B1 | 5/2001 | Beatty et al. |
| 6,292,702 | B1 | 9/2001 | King et al. |
| 6,315,778 | B1 | 11/2001 | Gambale et al. |
| 6,375,668 | B1 | 4/2002 | Gifford et al. |
| 6,468,272 | B1 | 10/2002 | Koblish et al. |
| 6,480,746 | B1 | 11/2002 | Ingle et al. |
| 6,500,174 | B1 | 12/2002 | Maguire et al. |
| 6,529,779 | B1 | 3/2003 | Sutton |
| 6,572,609 | B1 | 6/2003 | Farr et al. |
| 6,647,617 | B1 | 11/2003 | Beatty et al. |
| 6,673,290 | B1 | 1/2004 | Whayne et al. |
| 6,702,811 | B2 | 3/2004 | Stewart et al. |
| 6,786,905 | B2 | 9/2004 | Swanson et al. |
| 6,837,886 | B2 | 1/2005 | Collins et al. |
| 6,917,834 | B2 | 7/2005 | Koblish et al. |
| 8,157,796 | B2 | 4/2012 | Collins et al. |
| 8,249,685 | B2 * | 8/2012 | Falwell et al. .............. 600/374 |
| 2001/0007070 | A1 | 7/2001 | Stewart et al. |
| 2001/0025175 | A1 | 9/2001 | Panescu et al. |
| 2001/0047129 | A1 | 11/2001 | Hall et al. |
| 2002/0062124 | A1 | 5/2002 | Keane |
| 2002/0065459 | A1 | 5/2002 | MacAdam et al. |
| 2002/0091330 | A1 | 7/2002 | MacAdam et al. |
| 2002/0107511 | A1 | 8/2002 | Collins et al. |
| 2002/0169473 | A1 | 11/2002 | Sepetka et al. |
| 2002/0183638 | A1 | 12/2002 | Swanson |
| 2002/0188289 | A1 | 12/2002 | Hegde |
| 2003/0078574 | A1 | 4/2003 | Hall et al. |
| 2003/0093069 | A1 | 5/2003 | Panescu et al. |
| 2003/0114739 | A1 | 6/2003 | Fuimaono et al. |
| 2004/0044277 | A1 | 3/2004 | Fuimaono et al. |

FOREIGN PATENT DOCUMENTS

| | | |
|---|---|---|
| EP | 0 790 066 A2 | 8/1997 |
| EP | 0 982 047 A2 | 3/2000 |
| GB | 2271932 A | 4/1994 |
| JP | 54-150888 | 11/1979 |
| JP | 05-505118 | 8/1993 |
| JP | 11-500037 | 1/1999 |
| JP | 00-508561 | 7/2000 |
| JP | 01-509415 | 7/2001 |
| JP | 02-508989 | 3/2002 |
| JP | 03-513742 | 4/2003 |
| JP | 03-514612 | 4/2003 |
| WO | WO 93/16632 A1 | 9/1993 |
| WO | WO 94/00178 A | 1/1994 |
| WO | WO 94/06349 A1 | 3/1994 |
| WO | WO 94/16618 | 8/1994 |
| WO | WO 94/21165 A1 | 9/1994 |
| WO | WO 94/21167 A1 | 9/1994 |
| WO | WO 94/21168 A1 | 9/1994 |
| WO | WO 95/01751 A1 | 1/1995 |
| WO | WO 95/10319 A1 | 4/1995 |
| WO | WO 96/25097 | 8/1996 |
| WO | WO 97/17892 A1 | 5/1997 |
| WO | WO 99/05971 | 2/1999 |
| WO | WO 99/15225 A | 4/1999 |
| WO | WO 99/56812 A2 | 11/1999 |
| WO | WO 99/62413 A1 | 12/1999 |
| WO | WO 00/67656 A1 | 11/2000 |
| WO | WO 00/72909 A1 | 12/2000 |
| WO | WO 00/74555 | 12/2000 |
| WO | WO 01/17451 A1 | 3/2001 |
| WO | WO 01/82814 A2 | 11/2001 |
| WO | WO 01/95820 A | 12/2001 |
| WO | WO 02/087437 A | 11/2002 |
| WO | WO 02/087456 A | 11/2002 |
| WO | WO 02087679 | 11/2002 |
| WO | WO 2005/000841 A2 | 1/2005 |
| WO | WO 2005/112813 A1 | 12/2005 |

* cited by examiner

METHOD AND APPARATUS FOR MAPPING AND/OR ABLATION OF CARDIAC TISSUE

RELATED APPLICATIONS

This application is a continuation of U.S. application Ser. No. 11/596,403, entitled "Method and Apparatus for Mapping and/or Ablation of Cardiac Tissue", filed Jan. 11, 2008, which issued as U.S. Pat. No. 8,249,685 B2 on Aug. 21, 2012, which is a national stage PCT Application No. US2005/017337, filed May 17, 2005, which claims the benefit under 35 U.S.C. §119(e) to U.S. Provisional Application Ser. No. 60/571,821, entitled "Method And Apparatus For Mapping And/Or Ablation Of Cardiac Tissue," filed on May 17, 2004, each of which is herein incorporated by reference in its entirety.

BACKGROUND OF INVENTION

1. Field of Invention

The invention relates generally to medical devices for performing mapping and ablation procedures. More particularly, the invention relates to methods and apparatus for mapping and/or ablating cardiac walls.

2. Discussion of Related Art

The human heart is a very complex organ, which relies on both muscle contraction and electrical impulses to function properly. The electrical impulses travel through the heart walls, first through the atria and then the ventricles, causing the corresponding muscle tissue in the atria and ventricles to contract. Thus, the atria contract first, followed by the ventricles. This order is essential for proper functioning of the heart.

Over time, the electrical impulses traveling through the heart can begin to travel in improper directions, thereby causing the heart chambers to contract at improper times. Such a condition is generally termed a cardiac arrhythmia, and can take many different forms. When the chambers contract at improper times, the amount of blood pumped by the heart decreases, which can result in premature death of the person.

Techniques have been developed which are used to locate cardiac regions responsible for the cardiac arrhythmia, and also to disable the short-circuit function of these areas. According to these techniques, electrical energy is applied to a portion of the heart tissue to ablate that tissue and produce scars which interrupt the reentrant conduction pathways or terminate the focal initiation. The regions to be ablated are usually first determined by endocardial mapping techniques. Mapping typically involves percutaneously introducing a catheter having one or more electrodes into the patient, passing the catheter through a blood vessel (e.g. the femoral vein or artery) and into an endocardial site (e.g., the atrium or ventricle of the heart), and deliberately inducing an arrhythmia so that a continuous, simultaneous recording can be made with a multichannel recorder at each of several different endocardial positions.

When an arrythormogenic focus or inappropriate circuit is located, as indicated in the electrocardiogram recording, it is marked by various imaging or localization means so that cardiac arrhythmias emanating from that region can be blocked by ablating tissue. An ablation catheter with one or more electrodes can then transmit electrical energy to the tissue adjacent the electrode to create a lesion in the tissue. One or more suitably positioned lesions will typically create a region of necrotic tissue which serves to disable the propagation of the errant impulse caused by the arrythromogenic focus. Ablation is carried out by applying energy to the catheter electrodes. The ablation energy can be, for example, RF, DC, ultrasound, microwave, or laser radiation.

Atrial fibrillation together with atrial flutter are the most common sustained arrhythmias found in clinical practice. Current understanding is that atrial fibrillation is frequently initiated by a focal trigger from the orifice of or within one of the pulmonary veins. Though mapping and ablation of these triggers appears to be curative in patients with paroxysmal atrial fibrillation, there are a number of limitations to ablating focal triggers via mapping and ablating the earliest site of activation with a "point" radiofrequency lesion. One way to circumvent these limitations is to determine precisely the point of earliest activation. Once the point of earliest activation is identified, a lesion can be generated to electrically isolate the trigger with a lesion; firing from within those veins would then be eliminated or unable to reach the body of the atrium, and thus could not trigger atrial fibrillation.

Another method to treat focal arrhythmias is to create a continuous, annular lesion around the ostia (i.e., the openings) of either the veins or the arteries leading to or from the atria, thus "corralling" the signals emanating from any points distal to the annular lesion. Conventional techniques include applying multiple point sources around the ostia in an effort to create such a continuous lesion. Such a technique is relatively involved, and requires significant skill and attention from the clinician performing the procedures.

Another source of arrhythmias may be from reentrant circuits in the myocardium itself. Such circuits may not necessarily be associated with vessel ostia, but may be interrupted by means of ablating tissue either within the circuit or circumscribing the region of the circuit. It should be noted that a complete "fence" around a circuit or tissue region is not always required in order to block the propagation of the arrhythmia; in many cases simply increasing the propagation path length for a signal may be sufficient. Conventional means for establishing such lesion "fences" include a multiplicity of point-by-point lesions, dragging a single electrode across tissue while delivering energy, or creating an enormous lesion intended to inactivate a substantive volume of myocardial tissue.

U.S. Pat. No. 6,315,778 B1, entitled "Apparatus For Creating A Continuous Annular Lesion," which is herein incorporated by reference, discloses a medical device which is capable of ablating a continuous ring of tissue around the ostia of either veins or arteries leading to or from the atria. The medical device includes a protrusion that inserts into an ostium, thereby allowing electrodes to contact tissue near the ostium.

In some instances, it is desirable to perform mapping and/or ablation procedures on a cardiac wall (or other tissue) that is not located near an ostium. In such a scenario, the lack of a protrusion may help to allow electrodes of a device contact the cardiac wall or other tissue. In other cases, mapping and/or ablation may be desired at several locations around an ostium and it would be helpful to be able to position electrodes without concern for a protrusion that may hinder contact between electrodes and the cardiac wall.

SUMMARY OF INVENTION

Embodiments of the present invention encompass apparatus and methods for mapping electrical activity within the heart. Embodiments of the present invention also encompass methods and apparatus for creating lesions in the heart tissue (ablating) to create a region of necrotic tissue which serves to disable the propagation of errant electrical impulses caused by an arrhythmia. The apparatus and methods described herein also may be used for mapping and ablating of tissue other than heart tissue.

One embodiment of the invention is directed to a medical device for electrophysiology procedures, comprising a catheter shaft having a proximal end and a distal end. The braided conductive member is located at the catheter shaft distal end and the braided conductive member has an undeployed configuration in which the braided conductive member has a distal end and is in a longitudinally extended configuration. The braided conductive member further includes a deployed configuration in which the braided conductive member distal end is positioned proximally relative to portions of the to braided conductive member.

According to some embodiments, the braided conductive member comprises electrically conductive filaments. The braided conductive member may comprise mapping filaments and/or ablation filaments. In the deployed configuration, the braided conductive member may form a distally-facing surface with nothing protruding distally beyond the distally-facing surface.

According to some embodiments, the medical device further comprises a braided conductive member adjustment element constructed and arranged to move the braided conductive member distal end. The braided conductive member adjustment element may be a cable attached to the braided conductive member distal end, the cable being constructed and arranged to pull the braided conductive member distal end in a proximal direction. In the deployed configuration, the braided conductive member may form a distally-facing ring-shaped surface that is substantially perpendicular to a longitudinal direction of the braided conductive member. The medical device may further comprise a sheath that is advanceable over and retractable from the braided conductive member. the distal end of the catheter shaft may be steerable in some embodiments.

According to some embodiments, the medical device further comprises support elements within a proximal portion of the braided conductive member. The braided conductive member may be radially asymmetrically-shaped relative to a longitudinal axis of the braided conductive member. The braided conductive member may be longitudinally asymmetrically-shaped relative to a longitudinal axis of the braided conductive member. The medical device may further comprise a controller operatively connected to the braided conductive member. The medical device may further comprise an irrigation system.

According to a further embodiment of the invention, a catheter comprises a catheter shaft having a proximal end and a distal end, and a braided conductive member located at the catheter shaft distal end. The braided conductive member has an undeployed configuration in which a distal end of the braided conductive member is everted. The braided conductive member also has a deployed configuration in which a portion the braided conductive member is inverted.

In some embodiments, in the deployed configuration, the braided conductive to member forms a distal ring of filaments. In some embodiments, in the deployed configuration, nothing protrudes distally from the distal ring. In the deployed configuration, the distal ring may be arranged such that it contactable to a substantially flat area of tissue that has no ostia.

According to another embodiment of the invention, an apparatus comprises a catheter shaft having a distal end, and a braided conductive member disposed at the distal end of the catheter shaft. The braided conductive member comprises a plurality of filaments extending from a proximal anchoring location to a distal attachment location. The braided conductive member has a maximum diameter that is a first distance from the distal attachment location, the maximum diameter being a second, larger distance from the proximal anchoring location when the braided conductive member is in a relaxed state, and the distal attachment portion is retractable to radially expand the braided conductive member and to invert the braided conductive member.

According to yet another embodiment of the invention, an apparatus comprises a catheter shaft having a distal end, and a braided conductive member disposed at the distal end of the catheter shaft. The braided conductive member comprises a plurality of filaments extending from a proximal anchoring location to a distal attachment location, the braided conductive member having a maximum diameter that is longitudinally located more than two-thirds of the distance from the proximal anchoring location to the distal attachment location when the braided conductive member is in a relaxed state.

According to another embodiment of the invention, a method of positioning a braided conductive member within a patient comprises steps of introducing a braided conductive member into a patient in a first configuration in which a distal end of the braided conductive member is everted, and inverting the braided conductive member to place the braided conductive member in a second, deployed configuration in which the braided conductive member forms a distal annular surface with nothing protruding distally beyond the distal annular surface.

The method may further comprise retracting a sheath to expose the braided conductive member. In some embodiments, the step of inverting the braided conductive member distal end comprises actuating a braided conductive member adjustment element. Actuating the braided conductive member adjustment element may comprise pulling a cable attached to a distal end of the braided conductive member. In some embodiments, the method further comprises contacting the distal annular surface of the braided conductive member to cardiac tissue. The method may include detecting electrical impulses with the braided conductive member and transmitting the electrical impulses to a recording device. A step of activating a plurality of filaments that are part of the braided conductive member to ablate cardiac tissue may also be included as part of the method.

According to a further embodiment of the invention, a method of contacting cardiac tissue with a ring-shaped surface of a braided conductive member comprises steps of: introducing into a patient a catheter having a proximal end, a distal end, and a braided conductive member; configuring the braided conductive member such that it has a distally-facing, ring-shaped surface of filaments with nothing protruding distally from the distally-facing, ring-shaped surface; and contacting the distally-facing, ring-shaped surface to cardiac tissue.

The method may further comprise activating filaments of the braided conductive member to ablate the cardiac tissue and/or mapping electrical impulses with filaments of the braided conductive member.

BRIEF DESCRIPTION OF DRAWINGS

The accompanying drawings are not intended to be drawn to scale. In the drawings, like components that are illustrated in various figures are represented by a like numeral. For purposes of clarity, not every component may be labeled in every drawing. In the drawings.

DETAILED DESCRIPTION

Figure 1:
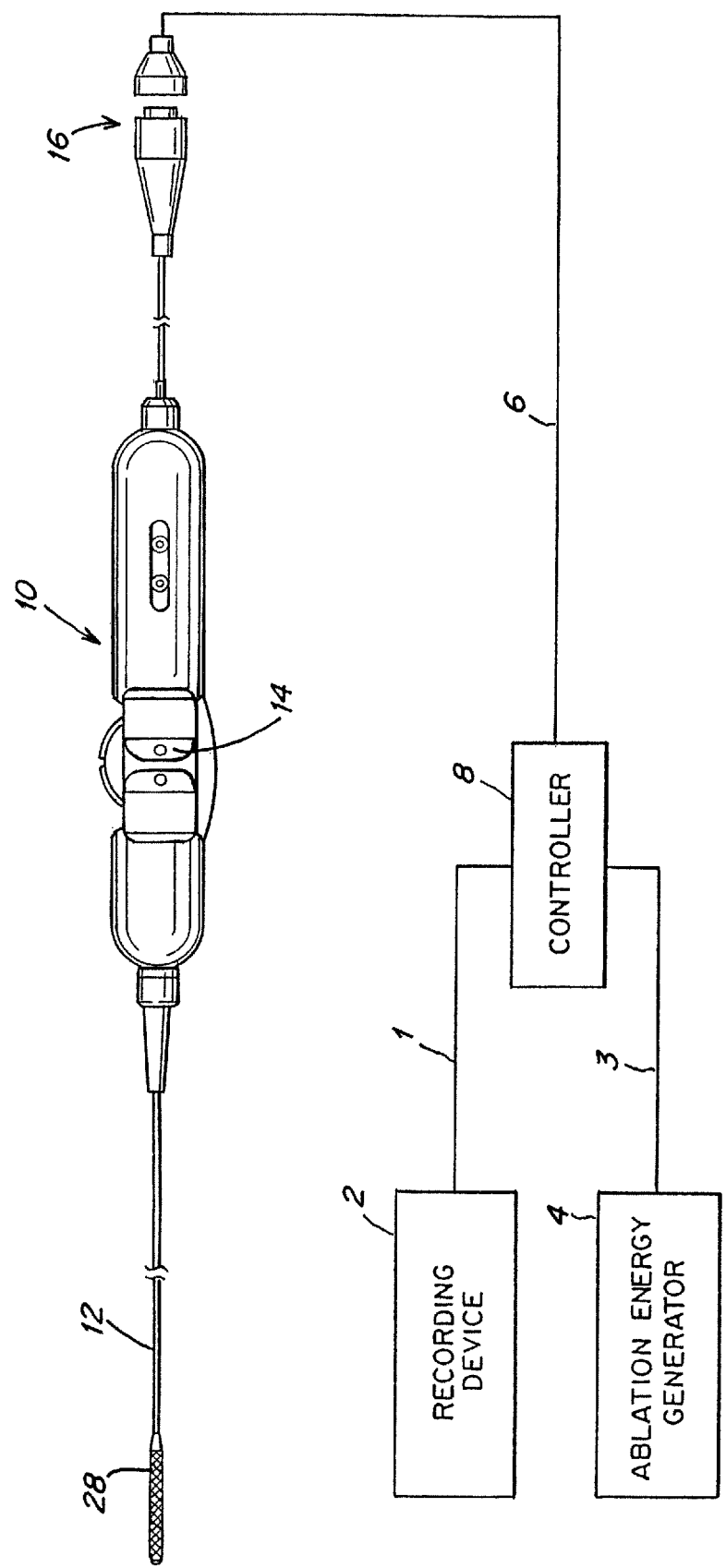
FIG. 1 illustrates an overview of a mapping and ablation catheter system in accordance with one embodiment of the present invention.

This invention is not limited in its application to the details of construction and the arrangement of components and acts set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

System Overview

Reference is now made to FIG. 1, which illustrates an overview of a mapping and/or ablation catheter system in accordance with one embodiment of the present invention. The system includes a catheter 10 having a shaft portion 12, a control handle 14, a connector portion 16, and a braided conductive member 28. A controller 8 is connected to connector portion 16 via cable 6. Ablation energy generator 4 may be connected to controller 8 via cable 3. A recording device 2 may be connected to controller 8 via cable 1. When used in an ablation application, controller 8 is used to control ablation energy provided to catheter 10 by ablation energy generator 4. When used in a mapping application, controller 8 is used to process signals coming from catheter 10 and to provide these signals to recording device 2. Although illustrated as separate devices, recording device 2, ablation energy generator 4, and controller 8 could be incorporated into a single device or two devices.

In this description, various aspects and features of the present invention will be described. The various features of the invention are discussed separately for clarity. One skilled in the art will appreciate that the features may be selectively combined in a device depending upon the particular application. Furthermore, any of the various features may be incorporated in a catheter and associated method of use for either mapping and/or ablation procedures.

Catheter Overview

Figure 2:
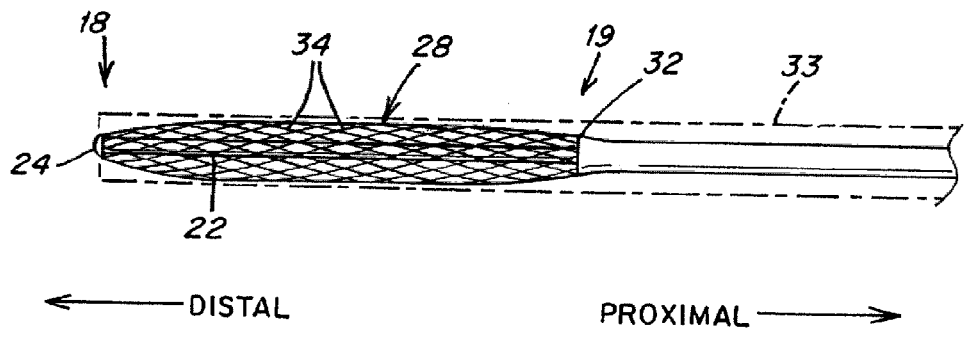
FIG. 2 illustrates a braided conductive member in an undeployed state according to one embodiment of the invention.
Figure 3:
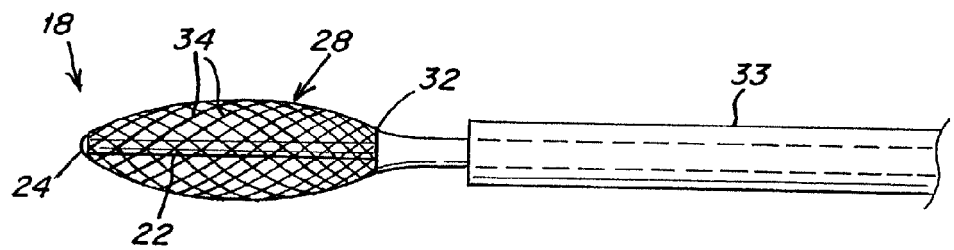
FIG. 3 illustrates a braided conductive member in a partially expanded state according to one embodiment of the invention.
Figure 4:
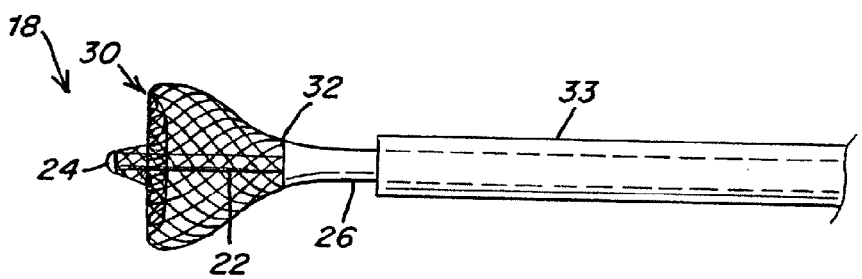
FIG. 4 illustrates a braided conductive member in an inverted state according to one embodiment of the invention.
Figure 5:
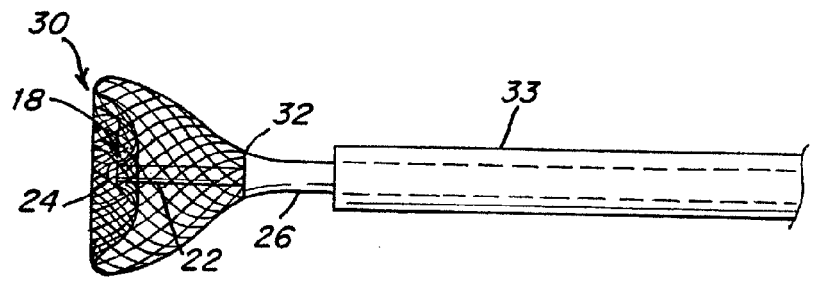
FIG. 5 illustrates a braided conductive member in an inverted state where a distal end of the braided conductive member does not protrude distally from the inverted braided conductive member according to one embodiment of the invention.

Reference is now made to FIGS. 2-5, which illustrate one embodiment of the present invention. Embodiments of the present invention generally include a catheter and methods of its use for mapping and ablation in electrophysiology procedures. FIG. 2 illustrates braided conductive member 28 in an unexpanded state. In this embodiment, the unexpanded state of the braided conductive member is an undeployed configuration. Braided conductive member 28 is, in one embodiment of the invention, a plurality of interlaced, electrically conductive filaments 34 which are attached at a distal end 18 with a cap 24 and also at a proximal end 19 with an anchoring element 32. Of course any suitable element or method may be used to attach or anchor filaments 34. FIG. 3 illustrates braided conductive member 28 in a partially expanded state. Each of FIGS. 2 and 3 show a state in which braided conductive member 28 is completely everted. FIG. 4 illustrates braided conductive member 28 in a first deployed configuration option which may be used to locate braided conductive member 28 at an ostium. In FIG. 4, distal end 18 of braided conductive member 28 is partially inverted. The terms "partially invert" and "partially inverted", for purposes herein, refer to a configuration in which portions of filaments are retracted within the braided conductive member such that they are at least partially surrounded by other portions of filaments. A tip, or other portions of the braided conductive member may protrude distally from any distally-facing surface of the braided conductive member when the braided conductive member is partially inverted. FIG. 5 illustrates braided conductive member 28 in a second deployed configuration option which may be used to effect contact between an annular surface of braided conductive member 28 and a cardiac wall (see, for example, FIG. 11) other cardiac tissue, or other target tissue. In FIG. 5, the distal tip of braided conductive member 28 is inverted. The terms "invert" or "inverted", for purposes herein, refer to a configuration in which the distal tip or distal end of the braided conductive member is retracted such that the distal tip does not protrude distally from a distally-facing surface of the braided conductive member. For purposes herein, the terms "evert" or "everted" refer to a configuration in which the distal tip or distal end of the braided conductive member protrudes distally from any distally-facing annular surface that is present. An everted configuration does not, however, require that a distally-facing annular surface be present. In some embodiments, such as the embodiment illustrated in FIG. 2, the braided conductive member is fully elongated in an everted configuration. The term "completely everted", when referring to a distal region of a braided conductive member, refers to a configuration in which no portion of the distal region of the braided conductive member is inverted within itself.

A braided conductive member adjustment element, such as a cable 22, is attached to distal end 18 of braided conductive member 28. Cable 22 may extend through a lumen (not shown) in shaft portion 12 and through the interior of braided conductive member 28. Cable 22 may be attached to distal end 18 of braided conductive member 28 using cap 24, an anchor band, or any suitable attachment or anchoring element or method known in the art. At the control handle end, cable 22 may be attached to a control element, such as a slide actuator for example, that allows a user to retract and advance cable 22. It should be noted that cable 22 is a separate element from cables 1, 3 and 6. Of course, braided conductive member adjustment element need not be a cable as any suitable element for adjusting the braided conductive member may be used. For example, a sheath may be used to push the braided conductive member over the distal tip of the braided conductive member to invert braided conductive member 28.

In operation, moving cable 22 in the proximal direction causes braided conductive member 28 to compress longitudinally and/or to expand radially, as shown in FIG. 3. Further proximal movement of cable 22 causes a portion of braided conductive to member 28 to invert as shown in FIG. 4. Even further proximal movement of cable 22 may retract distal end 18 such that distal end 18 is encircled by a portion of braided conductive member 28. In some embodiments, distal end 18 may be surrounded or partially surrounded by a portion of braided conductive member 28 that does not form a circle.

In some embodiments, a certain amount of movement of cable 22 in the proximal direction may occur without user actuation due to the bias of the braided conductive member 28. For example, braided conductive member 28 may be longitudinally extended beyond a relaxed state by radially compressing braided conductive member 28 with a sheath 33 (see FIG. 2). Upon retraction of sheath 33, braided conductive member 28 may radially expand a certain amount due to its filament winding structure, or due to elastic or spring elements attached to the filaments. In further embodiments, cable 22 may be used to urge braided conductive member 28 back into a longitudinally extended state by pushing on cap 24 or other distal attachment portion.

By retracting distal end 18 of braided conductive member 28 at least a certain distance in the proximal direction, a braided conductive member annular surface 30 may be formed in a plane that is substantially perpendicular to a distal end 26 of shaft portion 12, as illustrated in FIG. 4. Retracting distal end 18 further removes the projection of distal end 18 beyond annular surface 30, as illustrated in FIG. 5, which may allow annular surface 30 to be placed in contact with a cardiac wall or other cardiac tissue. If braided conductive member 28 is only partially inverted and distal end 18 projects beyond annular surface 30 in the distal direction, it may hinder efforts to contact cardiac tissue with the annular surface. In some embodiments, however, it may be desirable to maintain a portion of distal end 18 projecting from braided conductive member 28 so that braided conductive member 28 may be positioned relative to an ostium by inserting distal end 18 into the ostium. In some embodiments, the annular surface may be arranged such that it is contactable to a substantially flat area of tissue that has no ostia, even though an element may protrude distally from the annular surface. For example, a highly flexible element, such as a touch sensor, may protrude distally from the inverted braided conductive member and the annular surface would still be arranged such that it is contactable to a substantially flat area of tissue that has no ostia. The touch sensor may be a bend sensor that is positioned on the distal tip of the braided conductive member and protrudes slightly from the distally-facing surface when the braided conductive member is put into a deployed configuration. The bend sensor bends upon encountering a tissue wall and signals the controller that it has bent. The flexibility of the bend sensor allows the braided conductive member to contact the wall.

For purposes herein, a "surface" of braided conductive member 28 refers to a plurality of interlaced conductive elements, such as filaments or wires, even though the interlaced elements may not fully occupy the space considered to be the surface. In some embodiments, wires or other conductive elements may be attached to or embedded in a flexible support material such that a solid surface is present.

The annular surface formed by inverting the braided conductive member 28 may have electrodes spaced around the entire annular surface. In other embodiments, electrodes may be positioned only on a portion or portions of the ring-shaped surface.

As illustrated in FIGS. 2-5, a sheath 33 may be provided. Sheath 33 serves to protect shaft portion 12 and braided conductive member 28 during manipulation through the patient's vasculature. In addition, sheath 33 may shield braided conductive member 28 from the patient's tissue in the event ablation energy is prematurely delivered to the braided conductive member 28.

Sheath 33 may be advanced and retracted over shaft portion 12 in any suitable manner. Control handle 14 may be used to effect the advancement or retraction of sheath 33. U.S. Pat. Nos. 5,383,852, 5,462,527, and 5,611,777, which are herein incorporated by reference in their entireties, illustrate examples of control handles that can control sheath 33. As described in these patents, control handle 14 may include a slide actuator which is axially displaceable relative to the handle. The slide actuator may be connected to sheath 33 to retract sheath 33 to expose braided conductive member 28 once the distal end of the catheter has been positioned within the heart or other target location.

Braided conductive member 28 may be shaped or biased such that when sheath 33 is retracted, braided conductive member 28 expands slightly in the radial direction. In other embodiments, braided conductive member 28 may maintain its longitudinally extended shape until cable 22 or other adjustment element is pulled in the proximal direction to longitudinally compress braided conductive member 28. In still other embodiments, braided conductive member 28 may maintain a radial size similar to its relaxed state radial size when distal tip 18 is moved proximally, or even when braided conductive member 28 is inverted.

Braided conductive member 28 is, in one embodiment of the invention, a plurality of interlaced, electrically conductive filaments 34. In some embodiments, braided conductive member 28 is a wire mesh. The filaments 34 are preferably formed of metallic elements having relatively small cross sectional diameters, such that the filaments are flexible and the braided conductive member can be expanded radially outwardly. In one embodiment, the filaments may be round in cross-section, having a dimension on the order of about 0.001-0.030 inches in diameter. Alternatively, the filaments may have flat sides in cross-section, with thicknesses on the order of about 0.001-0.030 inches, and widths on the order of about 0.001-0.030 inches. The filaments may be formed of nitinol-type wire or other shaped memory alloys. Alternatively, the filaments may include non-metallic elements woven with metallic elements, with the non-metallic elements providing support to and/or separation of the metallic elements. A multiplicity of individual filaments 34 may be provided in braided conductive member 28, for example three hundred or more filaments. Instead of a multiplicity or plurality of filaments, a smaller number of filaments, or even only one continuous filament may be arranged to form braided conductive member 28. For purposes herein, the terms "filaments" or "plurality of filaments" may refer to one continuous filament that is interlaced with itself to form a braided conductive member.

Each of the filaments 34 may be electrically isolated from each other by an insulation coating. This insulation coating may be, for example, a polyamide type material. In one manner of forming an electrode, a portion of the insulation on the filaments forming an outer circumferential surface of braided conductive member 28 is removed. This arrangement allows each of the filaments 34 to form an isolated electrode, not in electrical contact with any other filament, that may be used for mapping and ablation. In some embodiments, an electrode may contact a coated section of another filament. Alternatively, specific electrodes may be permitted to contact each other to form a preselected grouping. Methods of removing insulation from filaments 34 are disclosed in PCT Publication No. WO 02/087437, which is herein incorporated by reference in its entirety. The insulation may also be removed in a preferential manner so that a particular portion of the circumferential surface of a filament 34 is exposed. In this manner, when braided conductive member 28 is radially expanded, the stripped portions to of filaments may preferentially face an intended direction of mapping or ablation.

Further, in some embodiments to the invention, some of filaments 34 may be used for mapping or electrical measurement, while others of filaments 34 may be used for ablation. The mapping and ablation filaments may be activated independently or may be activated concurrently. One application of dedicating some filaments for mapping and others for ablation is using a single braided conductive member 28 to both form a lesion and measure the quality of the lesion. Such an arrangement can avoid a change of catheters during a medical procedure. Temperature sensors (not shown) also may be included on catheter shaft 12 or braided conductive member 28.

A wire (not shown) may run from each of the filaments 34 to connector portion 16 via conductors (not shown). A multiplexer or switch box may be connected to the conductors so that each filament 34 may be controlled individually. This function may be incorporated into controller 8. In some embodiments, a number of filaments 34 may be grouped together for mapping and ablation. Alternatively, each individual filament 34 may be used as a separate mapping channel for mapping individual electrical activity at a single point. Using a switch box or multiplexer to configure the signals being received by filaments 34 or ablation energy sent to filaments 34 results in a large number of possible combinations of filaments for detecting electrical activity during mapping procedures and for applying energy during an ablation procedure.

Catheter 10 may also have a reference electrode (not shown) mounted on shaft 12 so that reference the reference electrode is located outside the heart during unipolar mapping operations.

Individual control of the electrical signals received from filaments 34 allows catheter 10 to be used for bipolar (differential or between filament) type mapping as well as unipolar (one filament with respect to a reference electrode) type mapping.

Catheter 10 may be a steerable device, in some embodiments, in that the distal end 26 may be deflected by an actuator contained within control handle 14. Control handle 14 may include a rotatable thumb wheel which can be used by a user to deflect distal end 26 of the catheter. The thumb wheel (or any other suitable actuating device) is connected to one or more pull wires (not shown) which extend through shaft portion 12 and connect to distal end 18 of the catheter at an off-axis location, whereby tension applied to one or more of the pull wires causes the distal portion of the catheter to curve in a predetermined direction or directions. U.S. Pat. Nos. 5,383,852, 5,462,527, and 5,611,777 illustrate various embodiments of control handle 14 that may be used for steering catheter 10.

Figure 6:
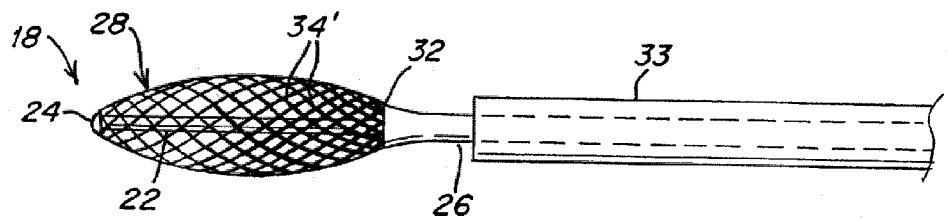
FIG. 6 illustrates a braided conductive member including support elements according to one embodiment of the invention.
Figure 7:
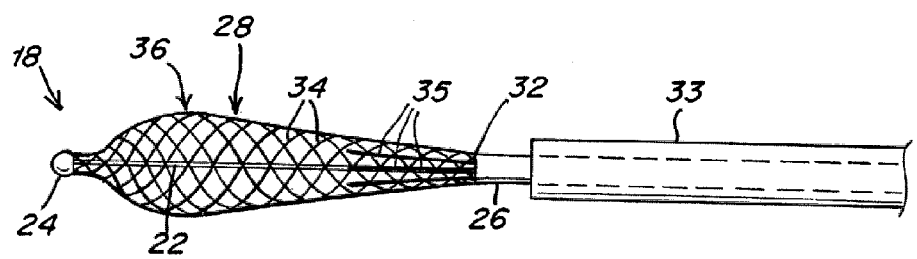
FIG. 7 illustrates a braided conductive member according to another embodiment of the invention.

In some embodiments, a proximal portion of braided conductive member 28 includes support elements to aid in maintaining the shape and/or structural integrity of portions of braided conductive member 28 when distal end 18 is moved in the proximal direction. For example, support elements may include support filaments 34' that are stronger, thicker or more rigid at their proximal ends than at their distal ends, as illustrated in FIG. 6. In other embodiments, splines 35 or other non-filament elements may be included, such as by interlacing support elements among filaments 34, as illustrated in FIG. 7. In still further embodiments, support elements which are not interlaced with filaments 34 may be included. In some embodiments, support elements attach to a proximal anchoring element 32 at a first end and to cap 24 or filaments 34 at a second end.

Referring to FIG. 7, an embodiment of the invention having a longitudinally asymmetrically shaped braided conductive member 28 is illustrated. In this embodiment, a maximum diameter 36 of braided conductive member 28 is located closer to distal end 18 than to proximal anchoring element 32. In one embodiment, maximum diameter 36 is longitudinally located more than two-thirds of the way from the proximal anchoring location to the distal attachment location. As cable 22 is drawn in the proximal direction to move cap 24, splines 35 support the more proximal region of braided conductive member 28.

Figure 8:
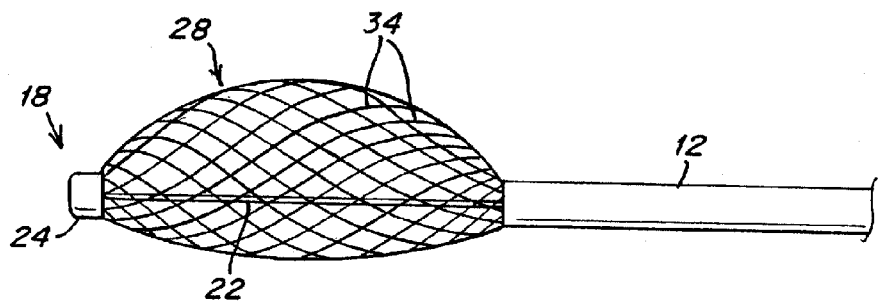
FIG. 8 illustrates an alternate embodiment of the braided conductive member according to another embodiment of the invention.

Reference is now made to FIG. 8 which illustrates another shape of braided conductive member 28. As described above regarding various embodiments of the invention, braided conductive member 28 may be generally radially symmetrical. However, certain anatomical structures may have complex three-dimensional shapes that are not easily approximated by a geometrically symmetrical mapping or ablation structure. To successfully contact these types of anatomical structures, braided conductive member 28 can be "preformed" to a close approximation of that anatomy, and yet still be flexible enough to adapt to variations found in specific patients. Alternatively, braided conductive member 28 can be of sufficient strength (as by choice to of materials, configuration, etc.) to force the tissue to conform to variations found in specific patients. For example, FIG. 8 illustrates braided conductive member 28 disposed about shaft 12 in an off-center or non-concentric manner such that braided conductive member 28 is radially asymmetrically-shaped. In addition, braided conductive member 28 may also be constructed so that the annular surface of the braided conductive member in its expanded configuration is a non-circular surface so as to improve tissue contact. FIG. 8 illustrates an example of this type of configuration where the braided conductive member 28 is constructed and arranged to be non-concentric with respect to a longitudinal axis of braided conductive member 28 and also, in its expanded configuration, to have an asymmetric shape. In some embodiments, the asymmetric expanded configurations and the eccentricity of braided conductive member 28 with respect to the longitudinal axis can be produced by providing additional structural supports in braided conductive member 28, for example, by adding nitinol wire, ribbon wire, splines, and so on. Other suitable methods of creating the eccentric and/or asymmetric shape include: varying the winding pitch; varying individual filament size and/or placement; deforming selective filaments in braided conductive member 28; and any other suitable method known to those skilled in the art.

An asymmetrically-shaped braided conductive member may allow for the formation of a ring-shaped surface that is disposed at an angle to general longitudinal direction of the braided member and/or the distal end of the catheter. The angled surface may permit better contact with certain tissue areas. In still other embodiments, inverting the braided conductive member may form a non-planar surface. For example, differing filament diameters may allow for the formation of a ring-shaped surface which includes a section that is substantially perpendicular to the catheter and a section that is disposed at an angle to the catheter. The angle of the surface relative to the catheter may change continuously across the surface in still other embodiments.

In some embodiments of the present invention, catheter 10 may be coated with a number of coatings that enhance the operating properties of braided conductive member 28. The coatings may be applied by any of a number of techniques and the coatings may include a wide range of polymers and other materials.

Braided conductive member 28 may be coated to reduce its coefficient of friction, thus reducing the possibility of thrombi adhesion to the braided conductive member as well as the possibility of vascular or atrial damage. These coatings can be combined with insulation (if present) on the filaments that make up braided conductive member 28. These coatings may be included in the insulation itself, or the coatings may be applied over the insulation layer.

Braided conductive member 28 also may be coated to increase or decrease its thermal conduction, which can improve the safety or efficacy of the braided conductive member 28. This change in thermal conduction may be achieved by incorporating thermally conductive elements or thermally insulating elements into the electrical insulation of the filaments that make up braided conductive member 28, or by adding a coating to the assembly. Polymer mixing, IBAD, or similar technology could be used to add Ag, Pt, Pd, Au, Ir, Cobalt, and others into the insulation or to coat braided conductive member 28.

In some embodiments, radioopaque coatings or markers may be used to provide a reference point for orientation of braided conductive member 28 when viewed during fluoroscopic imaging. The materials that provide radiopacity including, for example, Au, Pt, Ir, and others known to those skilled in the art. These materials may be incorporated and used as coatings as described above.

Antithrombogenic coatings, such as heparin and BH, can also be applied to braided conductive member 28 to reduce thrombogenicity to prevent blood aggregation on braided conductive member 28. These coatings can be applied by dipping or spraying, for example.

As noted above, the filament 34 of braided conductive member 28 may be constructed of metal wire materials. These materials may be, for example, MP35N, nitinol, or stainless steel. Filaments 34 may also be composites of these materials in combination with a core of another material such as silver or platinum. The combination of a highly conductive electrical core material with another material forming the shell of the wire allows the mechanical properties of the shell material to be combined with the electrical conductivity of the core material to achieve better and/or selectable performance. The choice and percentage of core material used in combination with the choice and percentage of shell material used can be selected based on the desired performance characteristics and mechanical/electrical properties desired for a particular application.

There may be times during ablation or mapping procedures when catheter 10 passes through difficult or tortuous vasculature. During these times, it may be helpful to have a guiding sheath (not shown) through which to pass catheter 10 so as to allow easier passage through the patient's vasculature.

Irrigation

Figure 9:
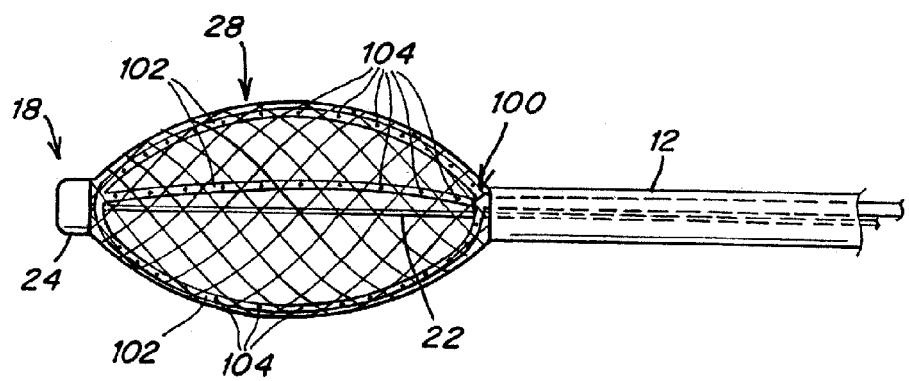
FIG. 9 illustrates the use of irrigation according to one embodiment of the invention.

It is known that for a given electrode side and tissue contact area, the size of a lesion created by radiofrequency (RF) energy is a function of the RF power level and the exposure time. At higher powers, however, the exposure time can be limited by an increase in impedance that occurs when the temperature at the electrode-tissue interface approaches a 100° C. One way of maintaining the temperature less than or equal to this limit is to irrigate the ablation electrode with saline to provide convective cooling so as to control the electrode-tissue interface temperature and thereby prevent an increase in impedance. Accordingly, irrigation of braided conductive member 28 and the tissue site at which a lesion is to be created can be provided in the present invention. FIG. 9 illustrates the use of an irrigation manifold within braided conductive member 28. An irrigation manifold 100 is disposed along shaft 12 inside braided conductive member 28. Irrigation manifold 100 may be one or more polyimide tubes. Within braided conductive member 28, the irrigation manifold splits into a number of smaller tubes 102 that are woven into braided conductive member 28 along a respective filament 34. A series of holes 104 may be provided in each of the tubes 102. These holes can be oriented in any number of ways to target a specific site or portion of braided conductive member 28 for irrigation. Irrigation manifold 100 runs through catheter shaft 12 and may be connected to an irrigation delivery device outside the patient used to inject an irrigation fluid, such as saline, for example, such as during an ablation procedure.

The irrigation system can also be used to deliver a contrast fluid for verifying location or changes in vessel diameter. For example, a contrast medium may be perfused prior to ablation and then after an ablation procedure to verify that there have been no changes in the blood vessel diameter. The contrast medium can also be used during mapping procedures to verify placement of braided conductive member 28. In either ablation or mapping procedures, antithrombogenic fluids, such as heparin can also be perfused to reduce thrombogenicity.

Figure 10:
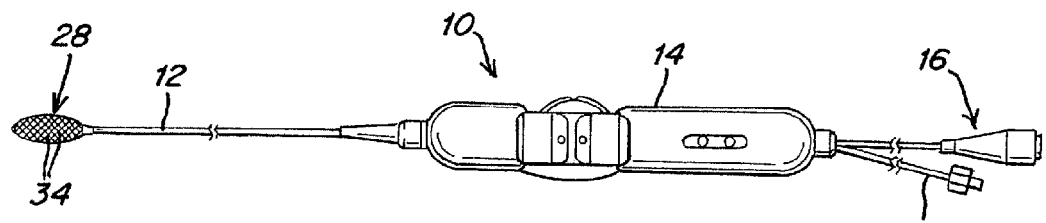
FIG. 10 illustrates the use of irrigation according to another embodiment of the invention.
Figure 10A:
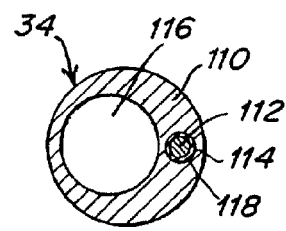
FIG. 10A is an enlarged cross-sectional view of a filament used in the braided conductive member illustrated in FIG. 10.

FIG. 10 illustrates another way of providing perfusion/irrigation in catheter 10. As illustrated in FIG. 10, the filaments 34 that comprise braided conductive member 28 may be composed of a composite wire 110. The composite wire 110 includes a lumen 114 containing an electrically conductive wire 112 that is used for delivering ablation energy in an ablation procedure or for detecting electrical activity during a mapping procedure. Composite wire 110 also contains a perfusion lumen 116. Perfusion lumen 116 is used to deliver irrigation fluid or a contrast fluid as described in connection with FIG. 9. Once braided conductive member 28 has been constructed with composite wire 110, the insulation 118 surrounding wire filament 112 can be stripped away to form an electrode surface. Holes can then be provided into perfusion lumen 116 to then allow perfusion at targeted sites along the electrode surface. As with the embodiment illustrated in FIG. 9, the perfusion lumens can be connected together to form a manifold which manifold can then be connected to, for example, perfusion tube 120 and connected to a fluid delivery device.

Methods of Use

Figure 11:
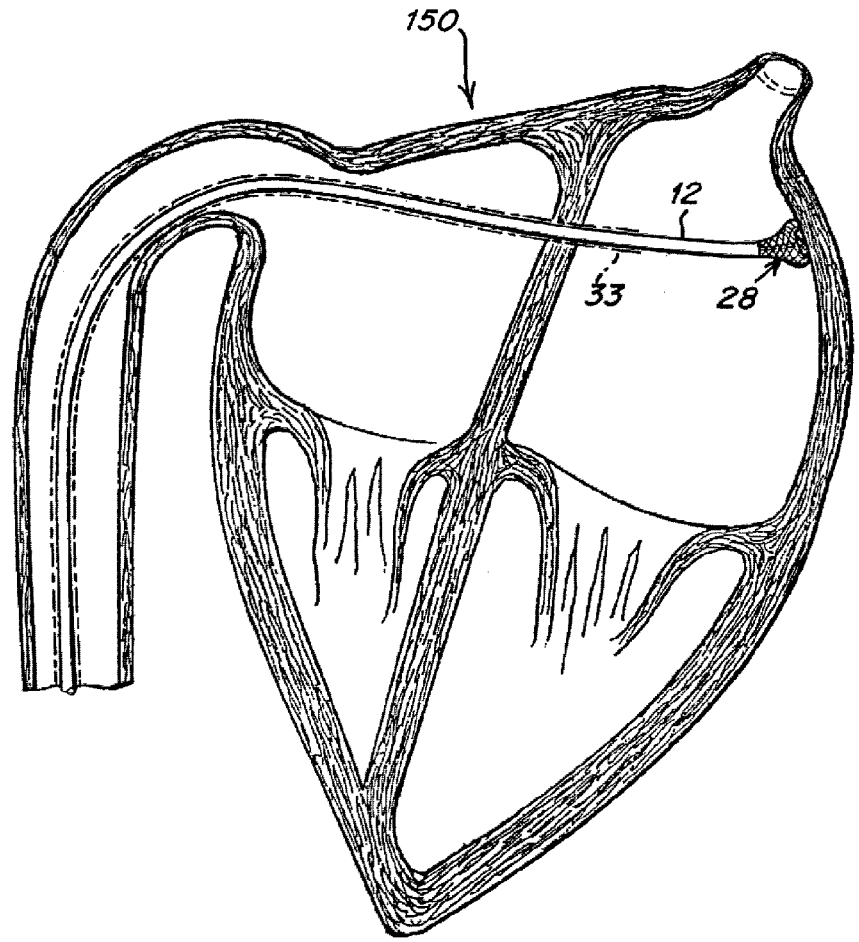
FIG. 11 illustrates one embodiment of a method of using a catheter and the braided conductive member.

Reference is now made to FIG. 11 which illustrates how a catheter according to certain embodiments of the present invention may be used in endocardial applications.

In an endocardial procedure, shaft portion 12 is introduced into a patient's heart 150. Appropriate imaging guidance (direct visual assessment, camera port, fluoroscopy, echocardiographic, magnetic resonance, etc.) can be used. FIG. 11 in particular illustrates shaft portion 12 being placed in the left atrium of the patient's heart. Once shaft portion 12 reaches the patient's left atrium, sheath 33 may be retracted and braided conductive member 28 may be inverted to its deployed state, where, in the illustrated embodiment, braided conductive member 28 forms a cone-type shape including a distally-facing, ring-shaped surface. External pressure may be applied along shaft portion 12 to achieve the desired level of contact between braided conductive member 28 and the cardiac tissue. In one embodiment, mapping of electrical impulses may be achieved with braided conductive member 28. In another embodiment, energy is applied to the cardiac tissue in contact with braided conductive member 28 to create an annular lesion. The energy used may be RF (radiofrequency), DC, microwave, ultrasonic, cryothermal, optical, etc.

In some embodiments, the braided conductive member may be configured such that it forms a distally-facing, ring-shaped surface before the braided conductive member is introduced to the heart.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A medical device for electrophysiology procedures, comprising:
    a catheter shaft having a proximal end and a distal end; and
    a braided conductive member located at the catheter shaft distal end;
    the braided conductive member having an undeployed configuration in which the braided conductive member has a distal end and is in a longitudinally extended configuration;
    the braided conductive member further having a deployed configuration in which the braided conductive member distal end is positioned proximally relative to portions of the braided conductive member; and
    a braided conductive member adjustment element configured to pull the distal end of the braided conductive member in a proximal direction to place the braided conductive member in to the deployed configuration; wherein
    in the deployed configuration, the braided conductive member forms a distally-facing ring-shaped surface and includes ablation electrodes configured to form an annular lesion in tissue when the distally-facing surface is contacted to the tissue and the ablation electrodes are activated.

2. A medical device according to claim 1, wherein the braided conductive member comprises electrically conductive filaments.

3. A medical device according to claim 1, wherein the braided conductive member comprises mapping filaments.

4. A medical device according to claim 1, wherein the ablation electrodes comprise ablation filaments.

5. A medical device according to claim 4, wherein the braided conductive member further comprises mapping filaments.

6. A medical device as in claim 1, wherein, in the deployed configuration, nothing protrudes distally beyond the distally-facing surface.

7. A medical device as in claim 1, wherein, in the deployed configuration, the braided conductive member forms a distal ring of filaments.

8. A medical device as in claim 1, wherein the braided conductive member adjustment element is a cable attached to the braided conductive member distal end, the cable being constructed and arranged to pull the braided conductive member distal end in a proximal direction.

9. A medical device as in claim 1, wherein, in the deployed configuration, the distally-facing ring-shaped surface is substantially perpendicular to a longitudinal direction of the braided conductive member.

10. A medical device as in claim 1, further comprising a sheath that is advanceable over and retractable from the braided conductive member.

11. A medical device as in claim 1, wherein the distal end of the catheter shaft is steerable.

12. A medical device as in claim 1, further comprising support elements within a proximal portion of the braided conductive member.

13. A medical device as in claim 1, wherein the braided conductive member is radially asymmetrically-shaped relative to a longitudinal axis of the braided conductive member.

14. A medical device as in claim 1, wherein the braided conductive member is longitudinally asymmetrically-shaped relative to a longitudinal axis of the braided conductive member.

15. A medical device as in claim 1, further comprising a controller operatively connected to the braided conductive member.

16. A medical device as in claim 1, further comprising an irrigation system.

17. A medical device as in claim 1, wherein the catheter shaft includes a lumen through which a cable is extendible.

18. A catheter comprising:
    a catheter shaft having a proximal end and a distal end; and
    a braided conductive member located at the catheter shaft distal end;
    the braided conductive member having an undeployed configuration in which a distal end of the braided conductive member is everted;
    the braided conductive member further having a deployed configuration in which a portion the distal end of the braided conductive member is inverted;
        wherein in the deployed configuration, the braided conductive member forms a distally-facing ring-shaped surface and includes ablation electrodes configured to form an annular lesion in tissue when the distally-facing surface is contacted to the tissue and the ablation electrodes are activated; and
    in the deployed configuration, nothing protrudes distally beyond the distally-facing ring-shaped surface.

19. A catheter as in claim 18, wherein, in the deployed configuration, the braided conductive member forms a distal ring of filaments.

20. A catheter as in claim 19, wherein, in the deployed configuration, the distal ring is arranged such that it contactable to a substantially flat area of tissue that has no ostia.

21. A catheter as in claim 18, wherein the catheter shaft includes a lumen through which a cable is extendible.

* * * * *